(12) United States Patent
Verderber

(10) Patent No.: US 7,690,807 B2
(45) Date of Patent: Apr. 6, 2010

(54) OPTICAL MIRROR ELEMENT

(76) Inventor: Gregory Rudolph Verderber, 8505 Fox Cub La., Cincinnati, OH (US) 45243

( * ) Notice: Subject to any disclaimer, the term of this patent is extended or adjusted under 35 U.S.C. 154(b) by 31 days.

(21) Appl. No.: 12/005,598

(22) Filed: Dec. 28, 2007

(65) Prior Publication Data
US 2009/0168409 A1 Jul. 2, 2009

(51) Int. Cl.
A61B 1/06 (2006.01)
(52) U.S. Cl. .................. 362/120; 362/572; 362/577; 362/800; 433/31
(58) Field of Classification Search ................. 362/409, 362/119, 120, 572, 573, 577, 559; 433/29-31
See application file for complete search history.

(56) References Cited

U.S. PATENT DOCUMENTS

| 1,281,136 | A |   | 10/1918 | Clement |
| 1,747,009 | A |   | 2/1930 | Jordan |
| 2,088,735 | A |   | 8/1937 | Everhards |
| 2,195,526 | A |   | 4/1940 | Traver |
| 2,393,319 | A |   | 1/1946 | Freedman |
| 2,428,975 | A |   | 10/1947 | Lamb |
| 3,032,879 | A |   | 5/1962 | Lafitte |
| 3,566,474 | A |   | 3/1971 | Zuhlke et al. |
| 3,638,013 | A |   | 1/1972 | Keller |
| 5,139,421 | A |   | 8/1992 | Verderber |
| 5,348,470 | A |   | 9/1994 | McGowan |
| 5,449,290 | A | * | 9/1995 | Reitz ........................... 433/31 |
| 5,457,611 | A |   | 10/1995 | Verderber |
| 5,951,142 | A | * | 9/1999 | Wang et al. ................. 362/109 |
| 6,443,729 | B1 |   | 9/2002 | Watson |
| 6,702,577 | B2 | * | 3/2004 | Wong ........................... 433/30 |
| 6,854,859 | B2 | * | 2/2005 | Cooper et al. ............... 362/139 |
| 7,066,734 | B1 |   | 6/2006 | Cooper |
| 7,099,732 | B2 | * | 8/2006 | Geng ........................... 700/117 |
| 7,371,066 | B2 | * | 5/2008 | Tamburrino et al. ........... 433/30 |
| 2002/0058230 | A1 | * | 5/2002 | Savin et al. .................... 433/31 |
| 2003/0207229 | A1 |   | 11/2003 | Wong |
| 2006/0014118 | A1 | * | 1/2006 | Utama ......................... 433/31 |

FOREIGN PATENT DOCUMENTS

DE 1932912 1/1971

OTHER PUBLICATIONS

"Light Piping with Lexan Resin" Lexan Technifacts, Dec. 1982, 3 pages.
"Mirolite (Registered) Lighted Mouth Mirror" The Butler Smile Factory, 1988, pp. 14 and 15.

* cited by examiner

Primary Examiner—Sandra L O'Shea
Assistant Examiner—Leah S Lovell

(57) ABSTRACT

The present invention consists of an optical mirror element to be used in combination with a light source. Light from a light source contained within the mirror element shank provides illumination in front of and behind the mirror head. In this way, for example, the invention can be used in dentistry both for illuminated, indirect vision in the mouth and as an illuminated cheek or tongue retractor. The invention can be used in combination with any suitable light source including, but not limited to, a conventional lamp, a light emitting diode, or a light pipe.

19 Claims, 2 Drawing Sheets

OPTICAL MIRROR ELEMENT

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The present invention relates to mirrors used for inspection and examination. More specifically, the invention relates to a dental optical mirror element to be used in combination with a handle and a light source.

Hand held dental mirrors have long been used in the field of dentistry and are well known to those skilled in the art. Dental mirrors are used to view areas of the mouth which are not easily viewable by direct line of sight.

Dental mirrors have been combined with a light source. Combining a dental mirror with a light source greatly increases the ability to view relatively dark areas of the mouth which are not visible by direct line of sight. Examples of such mirrors are disclosed in U.S. Pat. Nos. 1,747,009 to Jordan; 2,428,975 to Lamb; 3,638,013 to Keller; 5,139,421 to Verderber; 5,457,611 to Verderber; 6,443,729 to Watson; 6,702,577 to Wong and 7,066,734 to Cooper.

The illuminated dental mirror disclosed in U.S. Pat. No. 5,139,421 to Verderber is known to be the most successful illuminated mirror marketed to dentists. The Verderber mirror was long produced and marketed by Welch-Allyn, Inc., of Skaneateles, N.Y. and is currently produced and marketed by Integra LifeSciences Holdings Corporation's Miltex Dental business of York, Pa.

In U.S. Pat. No. 5,139,421 Verderber discloses a mirror element including a light transmitting shank. While the Verderber mirror has demonstrated commercial success, it is problematic; being relatively expensive to manufacture and relatively inefficient in terms of light transmission.

The shank of the Verderber mirror must be relatively thick in order to admit adequate light and transmit adequate light. As for example, the Verderber mirror is manufactured with a shank diameter of 0.25 inches. It has been discovered that a shank of this diameter is prone to gas bubble inclusions: after molten plastic is injected into a mold, the surface of the cylindrical shank hardens first. As the still molten plastic material within the shank cools, it shrinks, creating gas bubble inclusions. Gas bubble inclusions within the shank are a major fault as they interfere with light transmission and significantly reduce the efficiency of the instrument. To reduce the incidence of gas bubble inclusions within the shank of the Verderber mirror element, high mold pressure must be maintained and the shank must be cooled slowly. Operating an injection mold at high pressure reduces the life of the mold. Cooling the mold slowly increases the molding cycle time. Relatively short mold life and relatively slow molding cycles contribute significantly to the cost of manufacturing the Verderber mirror. It would be ideal to provide an optical mirror element having high quality light distribution, but which could be molded using low mold pressure and fast molding cycles.

The volume of plastic material comprising the shank of the Verderber mirror element accounts for about two thirds of the plastic material in the mirror element and is significant in terms of materials cost. Reducing the volume of plastic material comprising the shank of the Verderber mirror element would result in a considerable reduction in part cost. It would be ideal to provide a mirror element using a relatively small volume of plastic material, thereby significantly reducing the cost to produce said mirror element.

Some volume of light traveling through the shank of the Verderber mirror is lost as a result of interference with microbubbles and inclusions. As discussed in greater detail above, the Verderber shank is prone to gas bubble inclusions. Although high mold pressure and relatively slow molding cycles reduce the incidence of major gas bubbles, microbubbles are inevitably present within said shank. Further, inclusions of dust, oils and other unknown materials are inevitably present within said shank. A portion of the light transmitted through the shank strikes these inclusions and is thereby scattered, reducing the efficiency of the instrument. It would be ideal to provide a mirror element in which the distance light is transmitted through molded optical plastic is minimized.

BRIEF SUMMARY OF THE INVENTION

The present invention consists of an optical mirror element to be used in combination with a handle and a light source. The shank of the optical mirror element is a hollow cylinder or tube designed to accept and contain a light source. The invention can be used in combination with any suitable light source including, but not limited to a fiber optic light pipe, conventional lamp or a light emitting diode.

Light from a light source contained within the optical mirror element shank is directed toward a prism formed between the mirror head and the shank. Some light entering the prism is internally reflected and exits the face of the prism to provide illumination in front of the mirror head. Some light entering the prism exits the heel of the prism to provide illumination behind the mirror head. In this way, for example, the invention can be used in dentistry both for illuminated, indirect vision and as an illuminated cheek or tongue retractor.

In general, the object of the present invention is to provide a disposable optical mirror element having the high quality illumination characteristics of the mirror element disclosed in U.S. Pat. No. 5,139,421 to Verderber, but which is more efficient in terms of light transmission and which can be manufactured at lower cost.

An advantage of the present invention is that the optical mirror element described herein requires a relatively small volume of plastic material, thereby reducing the cost to manufacture the part.

A further advantage of the present invention is that it requires relatively thin wall sections, thereby allowing the optical mirror element to be molded using relatively fast molding cycles, further reducing the cost to manufacture the part.

A further advantage of the present invention is that it reduces light transmission through molded plastic material, thereby increasing the optical efficiency of the part.

These and other objects, features and advantages will become readily apparent from the following Detailed Description, which should be read in conjunction with the accompanying drawings.

BRIEF DESCRIPTION OF THE SEVERAL VIEWS OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION OF THE INVENTION

Figure 1:
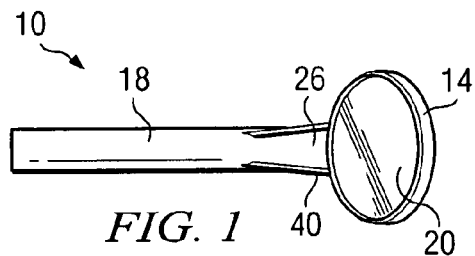
FIG. 1 is a frontal view of the optical mirror element.

For the purpose of promoting an understanding of the principles of the present invention, reference will now be made to the embodiments illustrated in the drawing (where like numerals indicate like elements of the invention) and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
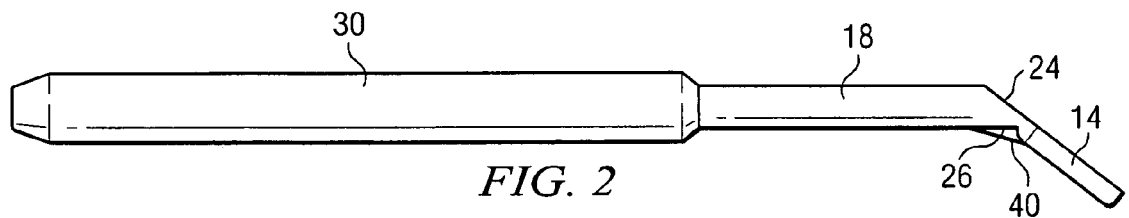
FIG. 2 is an elevation side view of the optical mirror element in combination with a dental mirror handle assembly.
Figure 3:
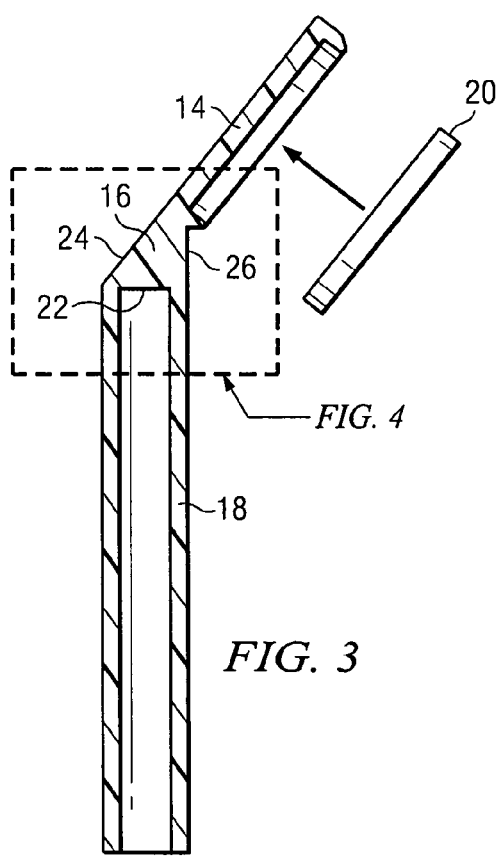
FIG. 3 is a cross-sectional side view of the optical mirror element specifically depicting the mirror head, prism, and shank.

An optical mirror element 10 is shown in FIGS. 1, 2 and 3. In FIG. 2 optical mirror element 10 comprises the distal portion of a dental mouth mirror. Optical mirror element 10 comprises three major segments, including, a head 14, a prism 16 and a shank 18.

Head 14, prism 16 and shank 18 are manufactured as a single unit from a light conductive material such as a plastic acrylic. Head 14 is generally disc-shaped and is inclined at a predetermined angle to shank 18. Within the front surface of mirror head 14, a recess is provided into which a conventional round mirror 20 may be inset or cemented as illustrated in FIG. 3. Alternately, a reflective material may be applied directly to the mirror head 14 such that said mirror head 14 can be used for indirect viewing.

Figure 4:
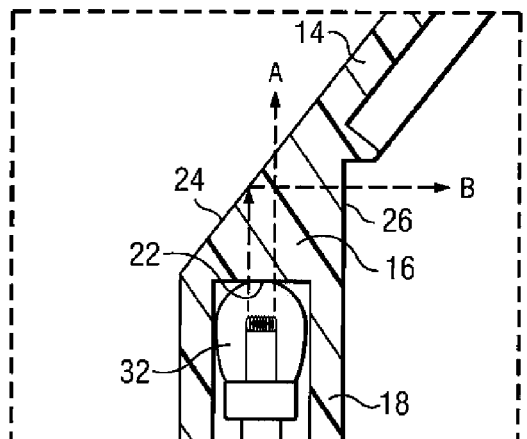
FIG. 4 is a partial view of the optical mirror element shown in FIG. 3 and in combination with a portion of a dental mirror handle assembly, specifically showing a light source of the dental mirror handle assembly contained within the shank of the optical mirror element and illustrating the optical effect of the prism of the optical mirror element.

Prism 16 is generally triangular in cross section as shown in FIGS. 3 and 4. Prism 16 forms the junction between the head 14 and the shank 18 and comprises three major segments, including a base 22, a heel 24 and a face 26. Referring now to FIGS. 3 and 4, face 26 is a flattened or planar surface at the junction of mirror head 14 and shank 18, and is generally parallel to the longitudinal axis of the shank 18. Heel 24 is a flattened planar surface at the junction of mirror head 14 and shank 18. Heel 24 is generally the same angle at which head 14 is inclined in relation to the longitudinal axis of shank 18. Base 22 is a flattened planar surface adjacent to said face 26 and said heel 24. Base 22 is generally perpendicular to face 26 and is inclined in relation to heel 18.

Figure 5:
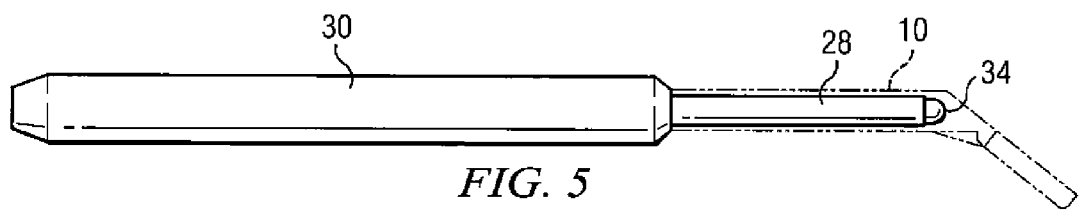
FIG. 5 is an elevation view of a dental mirror handle assembly including a light emitting diode, wherein an optical mirror element is shown in dashed lines to be removably inserted onto a male receptacle of the dental mirror handle assembly.
Figure 6:
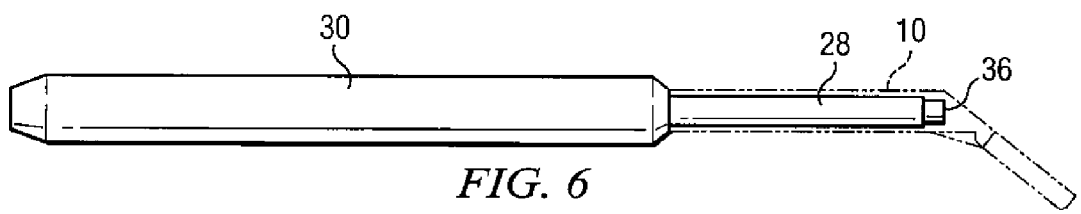
FIG. 6 is an elevation view of a dental mirror handle assembly including a fiber optic light pipe, wherein an optical mirror element is shown in dashed lines to be removably inserted onto a male receptacle of the dental mirror handle assembly.

Shank 18 is a hollow cylinder or tube having a proximal end and distal end. The proximal end of shank 18 terminates in the base 22 of prism 16. The distal end of hollow tubular shank 18 is open such that shank 18 can be removably inserted onto male receptacle 28 of handle 30 with the longitudinal axis of shank 18 parallel to the longitudinal axis of handle 30 as shown in FIG. 2. Optical mirror element 10 can be used with any suitable handle 30 having a light source. Said light source may be a conventional lamp 32 as shown in FIG. 4, light emitting diode 34 as shown in FIG. 5., or a fiber optic light rod 36 as shown in FIG. 6. Because the optical mirror element 10 described herein is separable from handle 30, said optical mirror element 10 can be easily and effectively sterilized, disinfected or replaced. When shank 18 is in place on handle 30, the base 22 of prism 16 is in close proximity to light source 32, 34, 36 comprising the distal end of male receptacle 28.

When the present invention is in use, light from said light source 32, 34, 36 is generally directed through the base 22 of prism 16. As for example, FIG. 4 shows a conventional lamp 32 contained within shank 18 where light is directed through the base 22 of prism 16 schematically illustrated by arrows representing light beams designated A and B. Light is transmitted through prism 16 with some volume of the light designated as A in FIG. 4 being emitted from heel 24 and some volume of light designated as B in FIG. 4 being internally reflected and emitted from face 26. The relative volume of light which is emitted from heel 24, or which is internally reflected and emitted from face 26, is a function of the critical angle of the material used for prism 16 and the angle of heel 24 in relation to the longitudinal axis of shank 18.

Varying the angle of heel 24 in relation to the longitudinal axis of shank 18 will cause more or less light to be directed in front of or behind mirror head 14, depending on the critical angle of the light conductive material utilized. Moreover, by varying the angle of heel 24 in relation to the longitudinal axis of shank 18, more or less light may be provided in front of mirror head 14 and a suitable mirror element 10 can be designed for specific needs.

Alternately, base 22 may be molded having a concave surface such that base 22 can be intimately mated with the curved surface of light source 32, 34, 36. Any or all surfaces of the prism including base 22, heel 24 and face 26 may be provided with a roughened or frosted surface thereby causing light applied to said prism to scatter creating a more uniform illumination pattern and eliminating halos.

Triangular supports 40 are provided between mirror head 14 and face 26 as shown in FIGS. 1 and 2 to increase the structural strength of the mirror element.

The hollow cylindrical shank 18, disclosed herein and shown in cross section in FIG. 3, reduces the volume of plastic material required to manufacture the mirror element 10 as compared with a mirror element having a solid shank. As for example, it is contemplated that the present invention will require fifty percent less plastic material as compared with the mirror element disclosed in U.S. Pat. No. 5,139,421 to Verderber. Reducing the volume of plastic required to manufacture optical mirror element 10 significantly reduces the cost of production.

Further, the hollow cylindrical shank 18 disclosed herein results in a mirror element 10 having relatively thin wall sections throughout. As for example the mirror element disclosed in U.S. Pat. No. 5,139,421 to Verderber has been manufactured having a solid cylindrical shank with an outside diameter of 0.25 inches. The present invention contemplates a hollow cylindrical shank 18, as shown in FIG. 3, having a 0.25 inch outside diameter with a wall thickness of 0.05 inches or less. The present invention, having relatively thin wall sections throughout, can be molded with faster molding cycles than the mirror element disclosed in U.S. Pat. No. 5,139,421 to Verderber, without resulting gas bubble inclusions, thereby significantly reducing the manufacturing cost.

Still further, the hollow cylindrical mirror element 10 shank 18 disclosed herein, wherein light source 32, 34, 36 is contained in close proximity to the mirror head 14, eliminates light transmission losses through said shank 18, thereby increasing the efficiency of the instrument. Micro-bubbles and other inclusions are inevitably present within an injection molded part, and as these inclusions decrease the efficiency of light transmission by means of scatter, the optical efficiency of an injection molded optical mirror element is directly related to the distance light must travel through the plastic material. As for example, the mirror element disclosed in U.S. Pat. No. 5,457,611 to Verderber has been manufactured having a shank length of about 1.75 inches, where light is transmitted through its entire length. The present invention contemplates a mirror element 10 where light would be transmitted through prism 16 having a maximum dimension of about 0.25 inches. The present invention therefore contemplates light transmission efficiency losses related to plastic inclusions to be about 0.25 inches divided by 1.75 inches or about one seventh that of the mirror element disclosed in U.S. Pat. No. 5,457,611 to Verderber.

The invention claimed is:

1. An optical mirror element, comprising:
   (a) a head comprising a forward surface and a rear surface, wherein at least one of the forward surface and the rear surface is mirrored;
   (b) a prism comprising a prism base, a prism heel and a prism face; and
   (c) a shank extending from a first end to a second end, each of the head and the prism being attached to the shank adjacent to the first end, at least one of the shank and the prism base defining an attachment means having a hollow bore, the second end of the shank defining an access opening to the hollow bore, and the hollow bore extending longitudinally within the shank from the access opening to the prism base;
   wherein the attachment means is configured to removably receive through the access opening and into the hollow bore an elongated male receptacle of a handle assembly, such that a light source at a distal end of the elongated male receptacle is in close proximity to the prism base, a first portion of light operably emitted from the light source is operably applied to the prism base for transmission through the prism base to the prism heel, and the first portion of light is operably internally reflected from the prism heel to the prism face and is operably emitted from the prism face adjacent to the head.

2. The optical mirror element of claim 1, wherein the head, the prism and the shank are a one-piece construction.

3. The optical mirror element of claim 1, wherein the prism face is adjacent to the forward surface of the head.

4. The optical mirror element of claim 3, further comprising at least one support between the prism face and the head.

5. The optical mirror element of claim 1, being configured such that a second portion of light operably emitted from the light source is operably applied to the prism base for transmission through the prism base to the prism heel and emission through the prism heel.

6. The optical mirror element of claim 5, wherein an amount of the first portion of light relative to an amount of the second portion of light depends at least partially upon an angle of the prism heel in relation to a longitudinal axis defined by the shank.

7. The optical mirror element of claim 1, wherein:
the shank has a shank length which is measured longitudinally from the first end to the second end;
the hollow bore has a bore length which is measured longitudinally from the access opening to the prism base; and
the bore length is greater than or equal to half of the shank length.

8. A mouth mirror, comprising:
a handle assembly comprising an elongated male receptacle and a light source, the elongated male receptacle extending longitudinally to a distal end, and the light source configured to emit light from the distal end; and
a removable optical mirror element comprising a head, a shank, and a face, the shank extending from a first end to a second end, the head comprising a mirrored surface and attached to the shank adjacent to the first end, the shank defining a hollow bore, the second end defining an access opening to the hollow bore, the hollow bore extending longitudinally within the shank from the access opening to a location adjacent to the head and the face;
wherein the elongated male receptacle is removably inserted into the hollow bore of the shank such that a portion of light operably emitted from the distal end of the elongated male receptacle passes through the face to provide illumination in front of the mirrored surface.

9. The mouth mirror of claim 8 wherein:
the optical mirror element further comprises a prism attached to the head and the first end of the shank;
the prism comprises the face, a base and a heel;
the base further defines the hollow bore in the shank; and,
the head, the shank and the prism are a one-piece construction.

10. The mouth mirror of claim 9 wherein the portion of light is operably applied to the base for transmission through the base to the heel, and wherein the portion of light is operably internally reflected from the heel to the face and is operably emitted from the face to provide the illumination in front of the mirrored surface.

11. The mouth mirror of claim 8 wherein the elongated male receptacle removably engages the shank of the optical mirror element.

12. The mouth mirror of claim 8 wherein the light source comprises at least one light emitting diode disposed at the distal end of the elongated male receptacle.

13. An optical mirror element, comprising:
a shank comprising an annular wall, the annular wall extending from a first end to a second end and defining a hollow bore, the hollow bore extending longitudinally within the shank from the first end of the annular wall to the second end of the annular wall, the first end of the annular wall defining an access opening to the hollow bore;
a face disposed adjacent to the second end of the annular wall; and
a head comprising a mirrored surface, the head being disposed adjacent to the face;
wherein the shank is configured to removably receive through the access opening and into the hollow bore an elongated male receptacle, such that a distal end of the elongated male receptacle is in close proximity to at least one of the face and the second end of the annular wall, and such that light emitted from the distal end operably passes through the face and provides illumination adjacent to the mirrored surface.

14. The optical mirror element of claim 13 wherein:

a shank length is measured longitudinally from the access opening to the head;

the shank length is about 1.5 inches to about 2.5 inches; and the hollow bore extends longitudinally within the shank along at least half of the shank length.

15. The optical mirror element of claim 13, wherein the annular wall has a wall thickness of less than or equal to about 0.05 inches, and wherein the annular wall has an outside diameter of about 0.25 inches.

16. The optical mirror element of claim 13 further comprising a prism disposed between the head and the second end of the annular wall, wherein:

the prism comprises the face, a base and a heel;

the base further defines the hollow bore;

the base is configured to receive and transmit the light from the elongated male receptacle to the heel; and the prism is configured to internally reflect the light from the heel to the face for transmission through the face to provide the illumination adjacent to the mirrored surface.

17. A mouth mirror, comprising:

an elongated male receptacle extending longitudinally to a distal end;

a light source fixedly positioned with respect to the elongated male receptacle and configured to emit light from the distal end of the elongated male receptacle; and an optical mirror element comprising a shank, a face, and a head, the shank comprising an annular wall, the annular wall extending from a first end to a second end and defining a hollow bore, the hollow bore extending longitudinally within the shank from the first end of the annular wall to the second end of the annular wall, the first end of the annular wall defining an access opening to the hollow bore, the face disposed adjacent to the second end of the annular wall, and the head comprising a mirrored surface and being disposed adjacent to the face;

wherein the elongated male receptacle is removably inserted into the hollow bore of the shank such that the light operably emitted from the distal end of the elongated male receptacle passes through the face to provide illumination adjacent to the mirrored surface.

18. The mouth mirror of claim 17 wherein the elongated male receptacle removably engages the shank of the optical mirror element.

19. The mouth mirror of claim 17 wherein the light source comprises at least one light emitting diode disposed at the distal end of the elongated male receptacle.

\* \* \* \* \*